(12) United States Patent
Wimmer

(10) Patent No.: US 6,699,183 B1  
(45) Date of Patent: Mar. 2, 2004

(54) QUICK-ACTING CLOSURE FOR AN ENDOSCOPE

(75) Inventor: Viktor Josef Wimmer, Seeon (DE)

(73) Assignee: XION GmbH, Berlin (DE)

( * ) Notice: Subject to any disclaimer, the term of this patent is extended or adjusted under 35 U.S.C. 154(b) by 0 days.

(21) Appl. No.: 09/786,654

(22) PCT Filed: Aug. 16, 1999

(86) PCT No.: PCT/DE99/02561

§ 371 (c)(1), (2), (4) Date: Jun. 21, 2001

(87) PCT Pub. No.: WO00/13569

PCT Pub. Date: Mar. 16, 2000

(30) Foreign Application Priority Data

Sep. 8, 1998 (DE) .......................... 198 40 986

(51) Int. Cl.[7] ................................. A61B 1/00
(52) U.S. Cl. ................. 600/147; 600/146; 600/149; 600/208; 600/104; 600/106
(58) Field of Search ................. 600/147, 146, 600/149, 152, 201, 208, 210, 219, 104, 106; 604/107, 108

(56) References Cited

U.S. PATENT DOCUMENTS

| 4,301,790 A | * | 11/1981 | Bol et al. ................. 600/152 |
| 4,686,965 A | * | 8/1987 | Bonnet et al. ............. 600/104 |
| 5,105,819 A | * | 4/1992 | Wollschlager et al. ...... 600/152 |
| 5,558,620 A | * | 9/1996 | Heckele et al. ............ 600/208 |
| 6,048,307 A | * | 4/2000 | Grundl et al. ............. 600/146 |
| 6,450,950 B2 | * | 9/2002 | Irion ..................... 600/146 |

FOREIGN PATENT DOCUMENTS

| EP | 0 609 503 A | 8/1994 |
| NL | 279 230 A | 3/1964 |

* cited by examiner

Primary Examiner—Sang Y. Paik  
Assistant Examiner—Fadi H. Dahbour  
(74) Attorney, Agent, or Firm—Shaffer & Culbertson, L.L.P.

(57) ABSTRACT

The invention relates to an endoscope comprising a first quick-acting closure (3) for a traction wire (13) of a Bowden wire device, which closure is arranged at the proximal end to be pivotable or displaceable, with a locking position of the quick-acting closure (3), in which an attachment unit for loosening and attaching the traction wire (13) of the Bowden wire device can be actuated and with a working position of the quick-acting closure (3), in which the attached traction wire of the Bowden wire device can be displaced within a working area which is defined by end positions (15', 15") of the quick-acting closure (3), in order to actuate a mechanism which is arranged at the distal end of the endoscope together with the traction wire (13) of the Bowden wire device in such a way that it can be loosened.

19 Claims, 7 Drawing Sheets

QUICK-ACTING CLOSURE FOR AN ENDOSCOPE

The invention relates to an endoscope, particularly a flexible endoscope with the features of the preamble of claim 1.

Endoscopes of this kind, for example duodenoscopes, whose lens is usually arranged at the side of the endoscope head, comprise a mechanism, in particular an Albarran mechanism with an Albarran lever, which makes it possible to move the probes, which are introduced into the endoscpoe through the working channel thereof, in the angle of view of the lens. The Albarran lever can be moved by means of a Bowden wire device extending between the distal and the proximal ends via an operating lever arranged at the outside of the endoscope's housing.

In commonly known endoscopes of the type described in the document U.S. Pat. No. 4,198,959, the Albarran mechanism or the Albarran lever is a fixedly integrated component of the endoscope head, and the sheathing of the Bowden wire device is embodied as a channel in the endoscope's introduction shaft and housing, which is sealed off from the inside of the endoscope. The traction wire of the Bowden wire device extending therethrough is usually sealed off from the outside at the distal and the proximal ends of the Bowden wire device with the aid of sealing rings. As these seals are seals through which a movable wire extends, at least the distal end may be contaminated as a result of pulling a piece of wire which is soiled e.g. with blood to the inside when an endoscope of this kind is used. Endoscopes or heads of endoscopes soiled in such a manner are difficult to clean and, when used again, lead to problems regarding hygiene or to spreading of germs and to increased sluggishness of the Bowden wire device or of the entire operating mechanism of the Albarran lever.

In another type of endoscope, the Bowden wire device can be irrigated for cleaning purposes through an opening for a syringe at the proximal end thereof. During irrigation, the liquid can emerge at the distal end of the Bowden wire device, which is not sealed. In case of inexpert handling, however, some of the irrigation liquid may leak into the inside of the endoscope as a result of too high pressure exerted on the inner seals. Mostly, such cases occurring in practice result from already existing contamination which causes a reduction of the cross-section of the channel to be irrigated and thus a lower rate of flow; here, the maximum permissible pressure may easily be exceeded if the operating personnel exerts too much pressure on the syringe. As a consequence of this, the endoscope will have to be repaired, which is both time-consuming and expensive.

Furthermore, both these known types share the disadvantage that the Albarran mechanism is difficult to clean because of the fact that it is integrated in the instrument. In practice, this mechanism has to be cleaned with a small brush, and it turned out that damage to the delicate Albarran mechanism is often caused thereby. Moreover, because of the integrated construction of the Albarran mechanism, any necessary repair thereof is time-consuming and expensive, as the entire encapsulated head, which also includes the lens, has to be exposed and, after the Albaran mechanism has been repaired, the head has to be encapsulated again.

In another endoscope known from the document JP Sho 62 42 606, the Albarran mechanism can be screwed off the endoscope head and can be removed after the traction wire of the Bowden wire device has been released at the proximal end by loosening a screw connection. After a distal stop plate has been loosened by screwing it off, the sheathing of the Bowden wire device can be pulled out.

This kind of loosening of the connection, however, requires technically skilled personnel—for reasons of liability, this is usually even done by a maintenance engineer of the company that produces the endoscope—, as such complex loosening of the connections can neither be expected from unskilled operating personnel such as a doctor's assistant nor can it be done by him or her.

If this endoscope should not have any seals to ensure that no contaminating material will enter at the distal end thereof, the endoscope would have to be cleaned after each use by loosening all the above-mentioned connections. As it is necessary to have this done by technically skilled personnel, this type of cleaning is complicated, expensive and time-consuming, and is thus not practical in medical working routine.

This problem was solved by an endoscope described in the document DE 196 27 016 C1; here, a support device for the Albarran mechanism can be removed from the head of the endoscope in the longitudinal direction by the operating personnel by loosening a quick-acting clamping device for the traction wire of the Bowden wire device, so both the support device, the traction wire of the Bowden wire device, the sheathing of the Bowden wire device, and the channel of the Bowden wire device can be cleaned easily by the operating personnel.

In practice, however, it turned out that a quick-acting clamping device which did not exist in known prior art was difficult to realize, as the necessary accuracy when moving a mechanism located at the distal end requires that the working area of the distal mechanism and the operating mechanism at the proximal end for this purpose always remains the same, irrespective of the number of loosening and attachment actions.

Thus, the object of the present invention is to provide an endoscope with a quick-acting clamping device which guarantees the required accuracy when moving a mechanism located at the distal end irrespective of the number of loosening and attachment actions, including the removal of the distal mechanism, pulling out the traction wire of the Bowden wire device and the sheathing thereof by the operating personnel, and easy loosening of the mechanism located at the distal end for cleaning purposes by the operating personnel.

According to the invention, this object is achieved by the features of claim 1.

By providing a quick-acting clamping device in the form of a quick-acting closure, with a locking position for loosening and attaching the traction wire of a Bowden wire device by means of an attachment unit, it is ensured that the attachment is always effected in the same exact position regarding the longitudinal displacement of the traction wire of the Bowden wire device. Hereby, the working area for the entire operating mechanism (both proximal and distal) for a mechanism to be operated, particularly an Albarran mechanism, remains the same at the distal end irrespective of the number of previous attachment and loosening actions.

At the same time, by providing a second quick-acting closure, it is possible for the operating personnel to easily remove the mechanism located at the distal end and to pull out the traction wire of the Bowden wire device. Thus, each time the endoscope has been used, it can easily be cleaned as necessary by the operating personnel. For this purpose, by loosening the first and the second quick-acting closures, the endoscope can quickly and easily be disassembled into the components traction wire of the Bowden wire device and distal mechanism; due to the fact that sealing elements are not necessary, all the contaminated parts as well as the inner space of the sheathing of the Bowden wire device can easily be cleaned by the operating personnel themselves, using e.g. effective cleaning and—as the case may be—sterilization methods such as ultrasonic waves, an autoclave, etc.

Furthermore, in case of wear, damage, etc., the Albarran mechanism can easily be replaced with a new Albarran mechanism by the operating personnel, potentially with further developments of Albarran mechanisms or other types thereof, without a time-consuming and expensive disassembly of the endoscope head and the proximal end of the endoscope by a technician being necessary.

If an individual channel of the Bowden wire device is formed inside the endoscope, as described in the document DE 196 27 016 C1, it is possible to additionally pull out the sheathing of the Bowden wire device and the traction wire of the Bowden wire device either at least partially or entirely. This further facilitates and improves the loosening of the Albarran mechanism and the support device and thus the cleaning of the Bowden wire device because now, with the separable connection for the traction wire of the Bowden wire device at the proximal end in the form of a first quick-acting closure, the entire Bowden wire device, i.e. the traction wire of the Bowden wire device and the sheathing thereof, can be pulled out either together or one after the other by at least a certain length or even completely.

Here, it is advantageous if, as described above, the sheathing of the Bowden wire device is not fixedly attached to the endoscope at the proximal and/or the distal end thereof, e.g. by a screw connection—although this is possible in principal—, but only limited in its movement in the longitudinal direction via a proximal and a distal stop, respectively. Here, the detachable support device may form the distal stop, so after loosening the traction wire of the Bowden wire device by the first quick-acting closure and after removing the support device by loosening the second quick-acting closure, it is possible to pull out not only the traction wire of the Bowden wire device, but also the sheathing of the Bowden wire device at the distal end in the longitudinal direction.

In an embodiment of the invention, the Albarran mechanism is located in a support device, which may be configured e.g. as a slide. This slide comprises guide elements which cooperate with complementary elements at the head of the endoscope in such a way that they prevent a lateral movement, i.e. perpendicularly to the direction of movement of the traction wire of the Bowden wire device. These guide elements may e.g. be configured as cylindrical projections which engage corresponding recesses at the head of the endoscope in the longitudinal direction, i.e. the direction of movement of the traction wire of the Bowden wire device. These projections may also be hollow cylindrical extensions of the channels present in the head of an endoscope, such as the channel of the Bowden wire device and/or the working channel for instruments to be introduced, which engage recesses in the distal end of the channels which have a correspondingly enlarged inner periphery. Of course, lateral guides extending in the longitudinal direction, such as a dovetail guide, are also conceivable. Advantageously, wrong insertion by the operating personnel and corresponding damage caused are avoided thereby, as the direction of insertion, which has to be effected substantially in the longitudinal direction because of the relatively rigid traction wire of the Bowden wire device, is predetermined thereby.

In a further embodiment of the invention, both the movement of the support device and the movement of the sheathing of the Bowden wire device in the longitudinal direction are prevented after insertion by the second quick-acting closure, having e.g. the form of a snap-fit or locking closure. Hereby, even in case of a sheathing of the Bowden wire device which is only fixed in the longitudinal direction in the form of proximal and distal stops or which is fixedly connected with the endoscope, it is possible to achieve an exact position of the traction wire of the Bowden wire device after insertion, with the Albarran mechanism or the Albarran lever being in its inoperative position. This inoperative position is reached automatically when the traction wire of the Bowden wire device is introduced into the sheathing of the Bowden wire device, due to the back pressure produced in the direction of the distal end; however, it can also be supported by a corresponding restoring spring at the Albarran lever.

In addition to the improved loosening of the Albarran mechanism and the support device and in addition to the advantages resulting therefrom, this embodiment of the invention also guarantees easier cleaning of the Bowden wire device and the channel of the Bowden wire device and of the areas which are otherwise very difficult to keep hygienically clean and sterile by the operating personnel, which cleaning has to be effected each time the endoscope has been used for reasons of hygiene.

In a further embodiment, the proximal end of the traction wire of the Bowden wire device is stiffened e.g. by soldering or by brazing, without increasing the outer periphery thereof. Advantageously, due to the increased resistance to pressure, this helps to avoid that the effect of attachment in the first quick-acting closure is impaired e.g. by squeezing, fraying out or destroying the end of the wire in any other way, without an undesired increase in the inner diameter of the sheathing of the Bowden wire device and also of a potentially existing additional channel of the Bowden wire device being necessary for introducing the traction wire of the Bowden wire device from the distal end.

In an advantageous embodiment of the invention, the arrested locking position and loosening or connecting the traction wire of the Bowden wire device with the first quick-acting closure can be achieved or effected simultaneously by means of a single operating element. For this purpose, the operating element is configured e.g. as a turning knob which comprises a characteristic guide line effective in the longitudinal direction and, in a plane perpendicular to this direction, an attachment mechanism affecting the wire for arresting. The attachment mechanism may be configured as an eccentric or cam rotatable in this plane, which affects the proximal end of the traction wire of the Bowden wire device directly or via a lever which has been prestressed by the force of a spring. Here, the characteristic guide line may be configured e.g. as a recess extending at the outer periphery and tapering in the direction of rotation towards the locking position, which cooperates with a peg which is fixedly arranged at the endoscope. By contrast, the end position "working area" in the opposite direction of rotation is formed by an opening which widens this recess in the longitudinal direction so that a peg fixedly arranged at the endoscope can be pivoted into the characteristic guide line or out of the same through this opening.

In a particularly advantageous embodiment of the invention, the quick-acting closure, which is configured e.g. as a pivotable flap, can be pivoted in one direction opposite to the distal end and beyond the working area, with the result that the traction wire of the Bowden wire device will slip through in the attachment unit by the length of this pivoting movement.

This may serve to exert a higher prestress onto the Bowden wire device in the direction of pushing if the shaft of the endoscope is in a position in which it is entwined and bent to a large extent, resulting in an imperfect restoring effect of the Albarran mechanism in its inoperative position. Thus, advantageously, the reduced working area occurring in known endoscopes in this position can be compensated, so the function and the mobility of the Albarran mechanism are not limited even in such a position. Instead of the action of slipping through, it is of course also possible to loosen the attachment unit in the quick-acting closure and to close it in a position differing from the former position or in a locking position, as described above. This makes it possible to, in a way, grasp the traction wire of the Bowden wire device again in both directions during an operation, so it is advantageously possible to react on working areas changed by extreme situations.

If the quick-acting closure which is arranged on the outside or is at least accessible from outside is pivoted in the longitudinal direction of the traction wire of the Bowden wire device, which means that it is merely displaced, the end of the traction wire of the Bowden wire device is advantageously not additionally subjected to a bending load. Thus, a potential breakage of the end of the traction wire of the Bowden wire device, particularly of a stiffened end, can be prevented.

If the quick-acting closure is configured as a clamping device which is displaceable in the longitudinal direction of the traction wire of the Bowden wire device, e.g. in the form of a slide with a clamping gripper which can be clamped or can be opened and closed by a clamping element, the end of the traction wire of the Bowden wire device is subjected to a force acting to the inside in an area within the clamping gripper from several sides distributed over the periphery or along the entire periphery or is clamped thereby. This has the advantage that damage resulting from a deformation or squeezing of a too small area or spot and/or a deformation of the cross-section of the traction wire from one side can be avoided.

What all the embodiments according to the invention have in common are advantages such as the exertion of a prestress, i.e. the change of the working area and the improved possibilities of cleaning by loosening and, as the case may be, disassembling of the quick-acting closures, removing the head of the endoscope and/or pulling out the Bowden wire device and, as the case may be, disassembling the same, and even a complete disassembly of all these parts by the operating personnel. Furthermore, the operating personnel themselves can easily attend to the maintenance, repair and exchange of individual parts, which could formerly only be done by a technician.

Further advantageous embodiments of the invention are apparent from the subclaims.

In the following, the invention is described in greater detail with the aid of embodiments illustrated in the drawing, in which.

Figure 1:
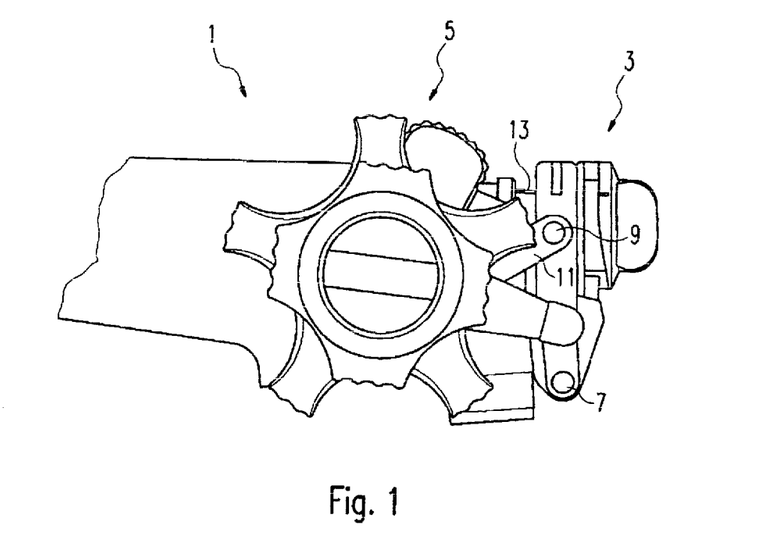
FIG. 1 shows a side view of a proximal end of an endoscope with a quick-acting closure.

The proximal end 1 of an endoscope, particularly a duodenoscope having a flexible endoscope shaft shown in FIG. 1, comprises a quick-acting closure 3 at the face thereof; in the lower portion thereof, this closure is pivotally mounted on the housing of the endoscope via an axle 7 e.g. in the form of one continuous shaft or two individual non-continuous bolts or screws. This quick-acting closure 3 in the form of a pivotable flap can be pivoted about the axle 7, which is perpendicular to the plane of the drawing, between a starting position and an end position by a lever mechanism which is pivotably connected with the closure in the upper portion of the quick-acting closure 3. In this way, a traction wire 13 of a Bowden wire device leading to the distal end, which traction wire is secured in the upper portion of the quick-acting closure, is displaced in its longitudinal direction perpendicular to the axle 7 and its rotational axis 7' in order to pivot a mechanism which is arranged at the distal end and is connected with the traction wire of the Bowden wire device, e.g. an Albarran lever 41 (FIG. 7), from its inoperative position into a working position.

Figure 2:
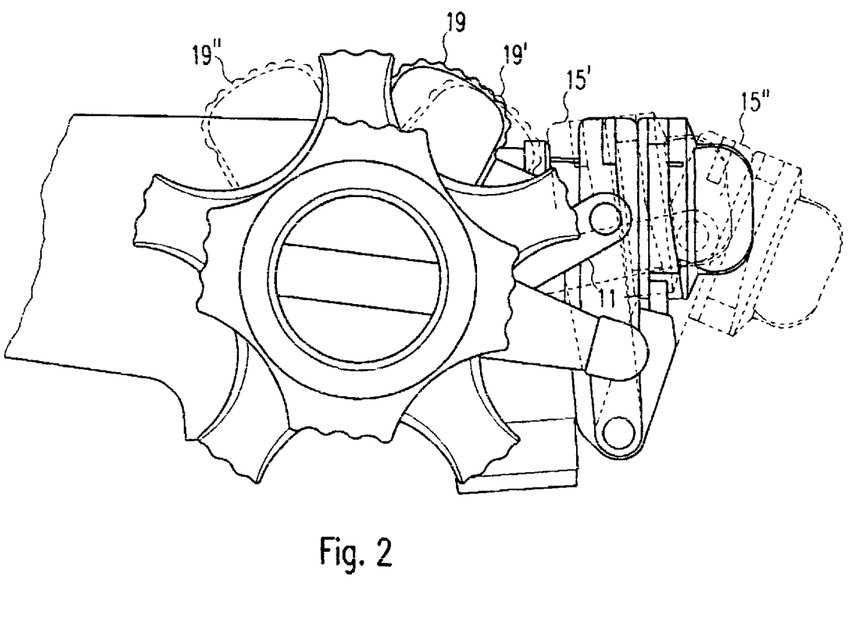
FIG. 2 shows an enlarged view according to FIG. 1 with the quick-acting closure in various positions.

The pivoting movement of the quick-acting closure from one end position 15' into another end position 15" is illustrated with a dashed line, respectively, in FIG. 2 as compared to the locking position which is illustrated with a normal line like in FIG. 1. Here, an operating lever 19 which is fixedly arranged at the housing of the endoscope in the area of a control mechanism 5 (shown in FIG. 1) for the movement of the flexible shaft and is rotatable about an axis that is perpendicular to the plane of the drawing, and which is pivotably connected with the lever 11 that is received at the quick-acting closure 3 so as to be rotatable about an axis that is perpendicular to the plane of the drawing, too, can be moved from a position 19' to a position 19" by the operating personnel until the end position 15', 15" of the quick-acting closure is reached.

Figure 3:
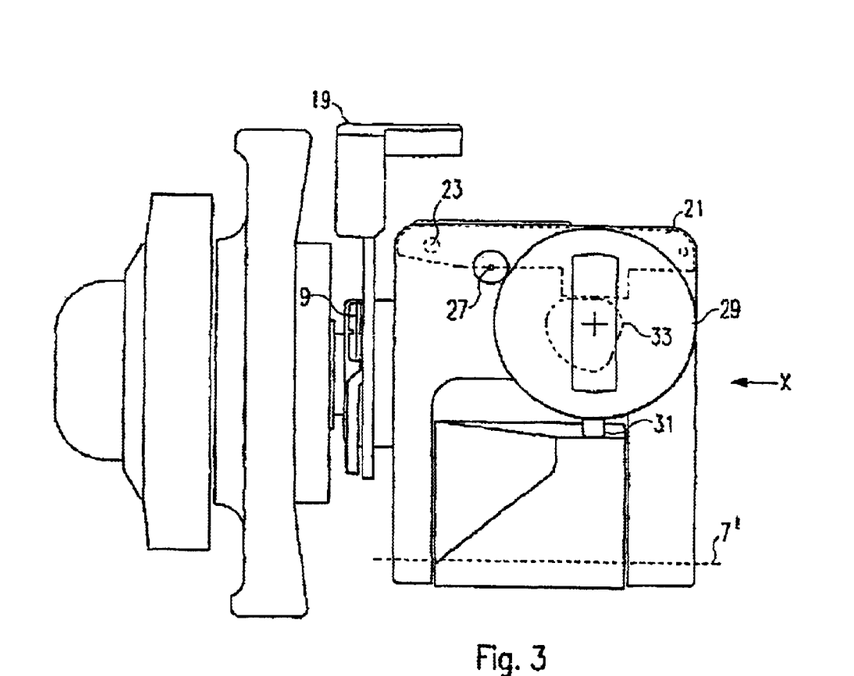
FIG. 3 shows a rear view according to FIG. 1.

As apparent from FIG. 3, a proximal end of the traction wire 13 (shown in FIG. 1) of the Bowden wire device is attached or loosened via a lever mechanism located in the upper portion of the quick-acting closure 3. This lever mechanism consists of a T-shaped lever 21 which is mounted in the quick-acting closure 3 in the plane of the drawing such that one end of its horizontal leg is pivotable about an axis that is perpendicular to this plane by means of a shaft or screw 23. At the opposite end of its horizontal leg, a restoring spring engages in a manner not shown in greater detail, whose other end is fixedly connected with a point 25 of the quick-acting closure 3 lying in an area beneath this lever (see FIG. 4).

Figure 4:
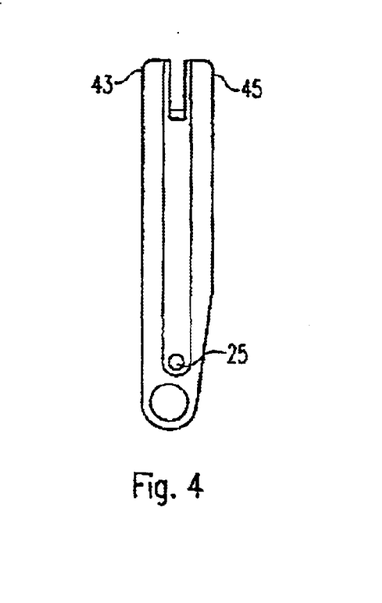
FIG. 4 shows an individual illustration of a flap of a quick-acting closure without a lever mechanism in a view X according to FIG. 3.

As illustrated in FIG. 3, an opening or hole 27 for the proximal end of the traction wire 13 of the Bowden wire device exists in the quick-acting closure 3 in the narrower portion of the fulcrum 23 of the lever 21, so the opening 27 lying in a plane perpendicular to the plane of the drawing is intersected by a lower edge of the lever 21 in the closer portion of the fulcrum 23. The line of direct connection between the fulcrum 23 and the hole 27 is markedly shorter than the line of connection between the fulcrum 23 and the working point of the restoring spring, whereby a lever action is created. In this way, as a result of this lever action, a force is exerted on an inserted end of a traction wire 13 which is larger than the restoring force of a spring arranged at the other end, so the traction wire 13 of the Bowden wire device in the opening 27 is clamped by the lever 21 in cooperation with the opening 27 through a front wall 43 and a rear wall 45 of the flap lying in one axis (FIG. 4). Of course, it is also conceivable that the lever 21 is arranged on the outside of the flap instead of being arranged between the front and the rear walls 43, 45 of the flap as in the embodiment serving as an example. In this case, however, the clamping effect on the traction wire 13 of the Bowden wire device is reduced because the traction wire is not clamped at two transitional portions any more, namely, the ones formed by the rear wall 45 and the lever 21 and by the lever 21 and the front wall 43, respectively, but at one transitional portion only.

The pivoting movement of the lever 21 is performed by an operating element in the form of a turning knob 29, which is pivotally mounted in the upper portion of the quick-acting closure beneath the lever 21 in a direction perpendicular to the plane of the drawing; the knob comprises an eccentric or cam 33 in the area of the lever 21 in the axis of rotation which is perpendicular to the plane of the drawing (FIG. 3), with the cam being fixedly arranged on the shaft of the turning knob 29. The peripheral surface of this cam 33 communicates with the lower end at the face of the lever 21, i.e. the vertical leg thereof, so when the cam 33 is rotated via the turning knob 29, the lever 21 can be swivelled from a lowermost to an uppermost position in the plane of the drawing (FIG. 3).

In the lowermost position shown in FIG. 3, in which the cam contacts the lever 21 with its smallest radius, the opening 27 is covered by the lever 21 and the traction wire 13 of the Bowden wire device is clamped thereby as described. Here, it is also conceivable that the cam 33 does not contact the lower face of the lever 21 with its peripheral surface any more. However, if the cam 33 is moved by the turning knob 29 into a position in which its peripheral surface contacts the lower face of the lever 21 with a larger or even the largest radius, the lever 21 is deflected from the position described, whereby the opening 27 is exposed, so that the proximal end of a traction wire 13 can be introduced into or pulled out of the same.

The traction wire 13 of the Bowden wire device can both be attached and clamped in the position of the quick-acting closure 3 illustrated in FIG. 1. In order to securely ensure that this position remains fixed, a recess is provided at the outer periphery of the turning knob 29, whose width in relation to the axis of rotation decreases towards an end point and which has a uniform depth, with this recess having the form of a volution 35 shown in FIG. 5a. At its starting point, this volution comprises an entrance in the form of an opening, so it opens to the underside of the turning knob 29.

At its thinnest end position, the volution 35 has a thickness which roughly corresponds to the diameter of a peg 31 fixedly arranged at the housing of the endoscope, with the peg engaging the volution in its plane, i.e. the plane of the drawing according to FIG. 3, in a locking position of the quick-acting closure 3.

Figure 5A:
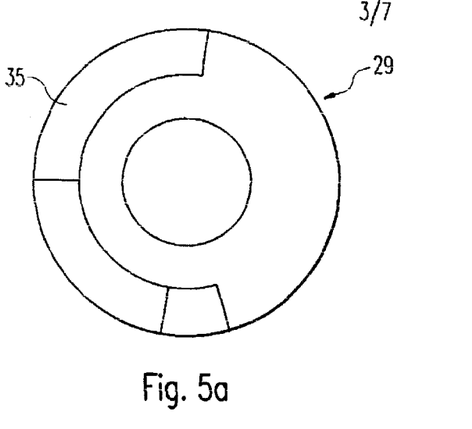
FIGS. 5a–e show different views of a turning knob of a quick-acting closure.
Figure 5B:
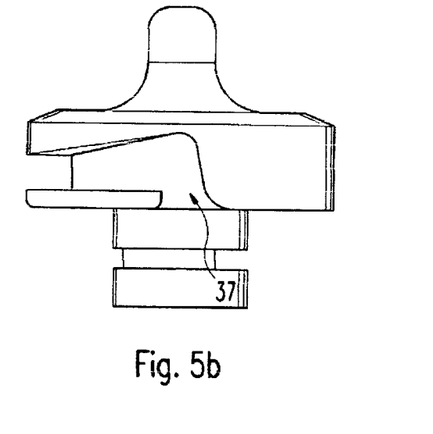

The opening 37 (shown in FIG. 5b of the volution 35, however, is somewhat larger than the diameter of the peg 31 so that the peg can be introduced into the profile of the volution more easily and a movement of the flap between the end positions 15' and 15" can be ensured in a working position of the turning knob 29 with the traction wire 13 of the Bowden wire device being clamped. As apparent from FIG. 5b, the entrance opening can be widened towards the underside of the turning knob 29 in order to introduce the peg 31 more easily.

Figure 5C:
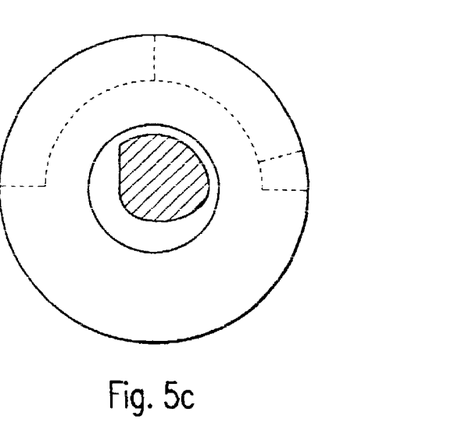
Figure 5D:
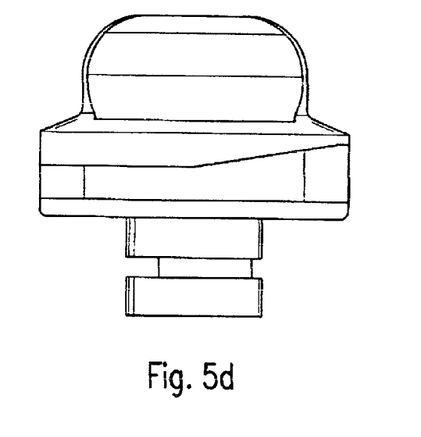
Figure 5E:
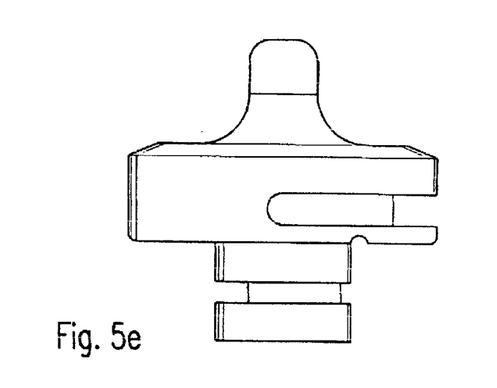

As can be seen from FIGS. 5a and 5c, the profile of the volution extends over a 180° portion of the outer periphery of the turning knob 29, with other portions—e.g. from 60° to 360°, being conceivable, too. The size of the portion only depends on the cooperation with the cam 33 and additionally, as the case may be, on the operating convenience. Depending on the point at which the peg 31 engages the entrance of the profile of the volution, the cam has to contact the lever 21 at the lower face thereof with its smallest radius in order to clamp the end of the traction wire 13 of the Bowden wire device and to ensure a free pivoting movement of the quick-acting closure 3. However, at the point at which the peg 31 engages the thinnest portion of the profile of the volution, the cam has to contact the lower face of the lever 21 with its largest radius in order to particularly ensure that, when the quick-acting closure is arrested in its locking position (FIG. 1), the wire 13 is introduced and clamped at a predetermined invariable position. For this purpose, as illustrated in FIG. 5a, the volution may comprise a larger portion 35, e.g. 90°, of the smallest thickness within which the wire 13 is released via the cam 31 and the lever 21 until it is clamped thereby, with the quick-acting closure 3 being fixed or arrested in its locking position as a result of the engagement of the pin 31 in this portion 35 without any clearance.

This has the advantage that an operating error, such as clamping the traction wire 13 of the Bowden wire device in a wrong position of the quick-acting closure 3 resulting in a limited or wrong working area for the mechanism at the end of the endoscope which is to be actuated via the Bowden wire device, e.g. an Albarran lever 41 (shown in FIG. 7), can be avoided.

As apparent from FIG. 2, the predetermined locking position of the quick-acting closure does not correspond to its end position 15', but to a position (FIG. 1) which is slightly remote from this end position 15' in the embodiment serving as an example. In this way, a small prestress can be exerted on the Bowden wire device in order to compensate e.g. a small clearance that might be present between the traction wire 13 of the Bowden wire device and the sheathing of the Bowden wire device, as it might otherwise happen that an end position of the mechanism at the distal end in the direction of pushing cannot be reached. The resulting greater length of the traction wire 13 in the Bowden wire device can be compensated in the other end position 15", i.e. in the direction of pulling, by the small displacement thereof in the direction of pulling and the working area slightly widened thereby.

In some cases of application, the flexible endoscope shaft has to be bent and/or twisted in such a way that the friction between the traction wire of the Bowden wire device and the sheathing of the Bowden wire device is increased to such an extent that the normal length of the traction wire 13 of the Bowden wire device is not sufficient to bring the distal mechanism in its end position in the direction of pushing. In this position, the traction wire 13 of the Bowden wire device fills any clearance that is present in the sheathing of the Bowden wire device because of the extreme curvature of the Bowden wire device.

In order to guarantee full freedom of motion in this extreme position, as well, the quick-acting closure can be pivoted beyond its normal end position 15''' by the operating personnel—necessarily with the application of a higher physical force than usual—, and in spite of being clamped, the traction wire 13 of the Bowden wire device slips out of the attachment in the hole 27 by the amount of this movement exceeding the end position 15". This slipping out or slipping through can be made possible by adjusting a corresponding clamping force at the restoring spring and/or by the cooperation of cam and lever 21 and the resulting overlapping of the hole 27, without limiting the function of the Bowden wire device, for example by undesired slipping of the wire 13 in the quick-acting closure.

Hereby, an even larger prestress can be exerted upon the Bowden wire device and an even larger portion of the wire can be brought into the Bowden wire device, so even in these extreme positions of the endoscope shaft and thus of the Bowden wire device provided inside, the full freedom of motion of the mechanism at the distal end is guaranteed.

Figure 6:
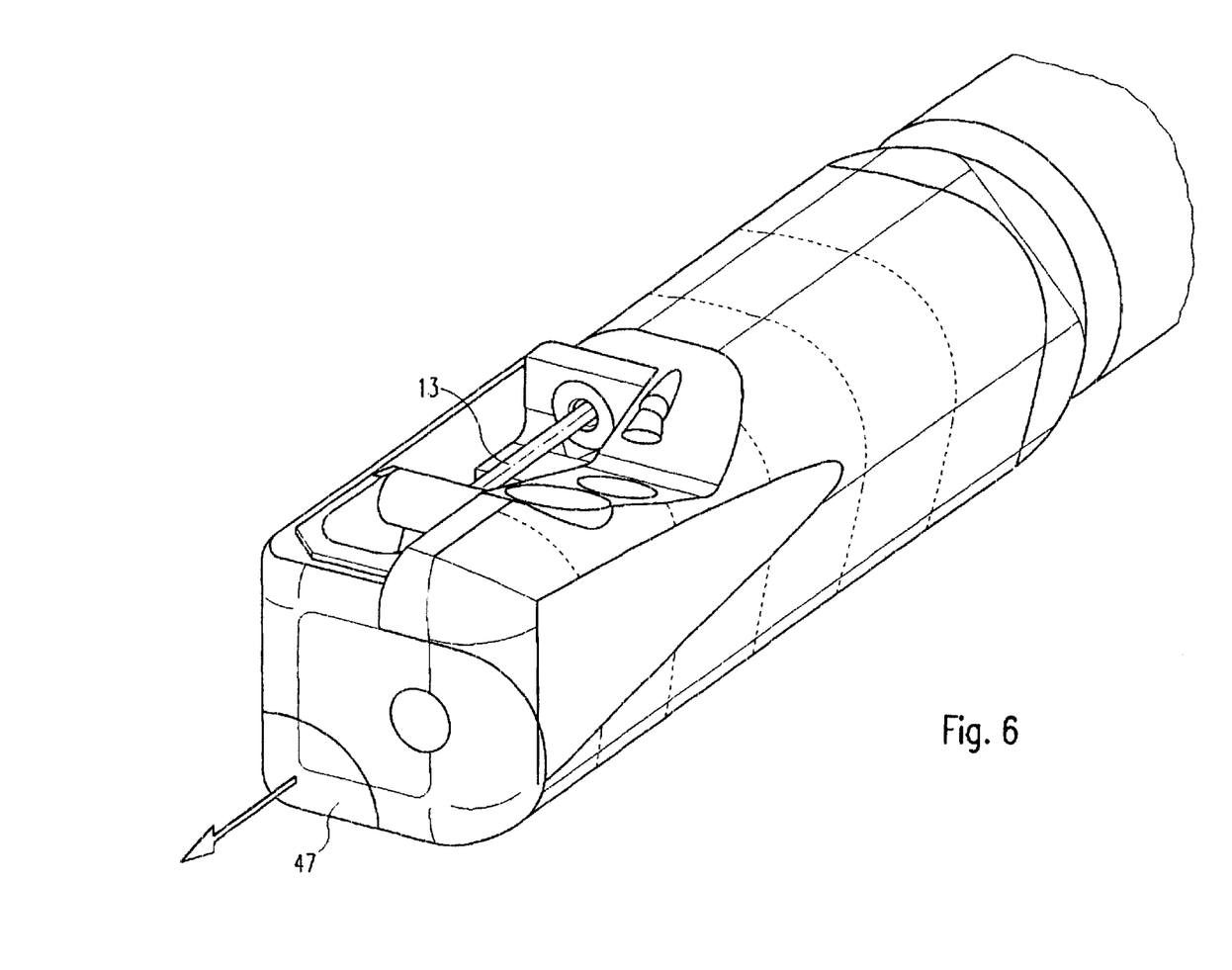
FIG. 6 shows a perspective view of a distal end of an endoscope.
Figure 7:
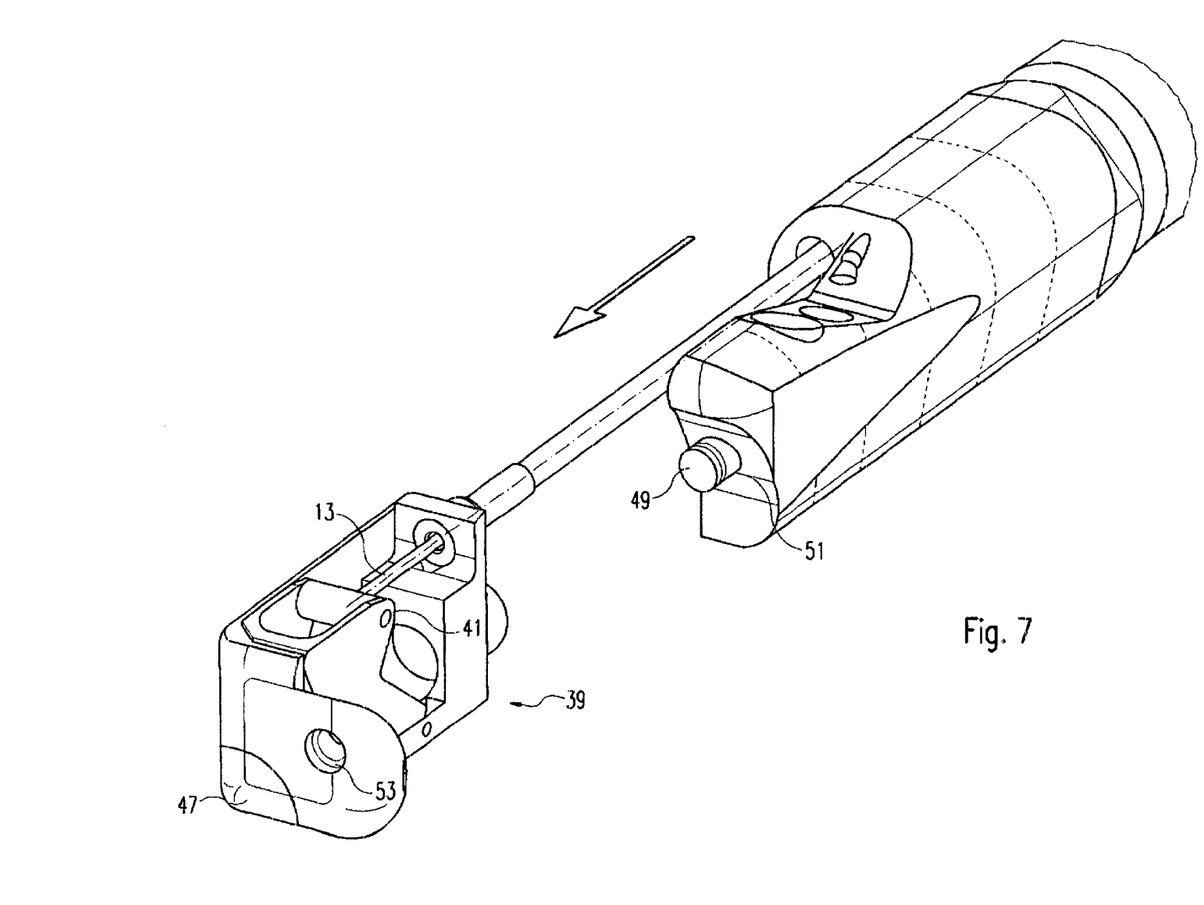
FIG. 7 shows the distal end of an endoscope according to FIG. 6, with the support device being removed.

FIGS. 6 and 7 show how a mechanism in a support device 39 at the distal end of the endoscope can be detached from the head of the endoscope.

For this purpose, it is only necessary for the operating personnel to actuate a quick-acting closure via a key 47 at the head of the endoscope, e.g. at the face thereof in a corner portion of the support device, after the quick-acting closure 3 has been brought into a release position for the traction wire 13 at the proximal end. Here, the quick-acting closure at the distal end can be configured e.g. as a recess of the endoscope head, in which an engagement element in the support device 39, which is complementary thereto and which can be actuated by the operating personnel, engages in the position shown in FIG. 6. As shown in FIG. 7, this recess may be configured as a groove 51 in a peg 49 projecting in the longitudinal direction and may e.g. extend around the periphery thereof, so that this peg 49 can engage a corresponding recess in the support device 39. When the support device has been put on (FIG. 6), an engagement element 53 which can be actuated from outside by the operating personnel via the key 47 engages this groove 51 in a plane perpendicular to the longitudinal axis of the peg 49 so that the support device 39 is fixedly secured to the head of the endoscope. For this purpose, the engagement element 53 may be configured e.g. as an apertured plate which is pressed into the direction of engagement or is prestressed by the force of a spring in such a way that a part of the edge of the hole engages the groove 51 and can be disengaged from this engagement position via the key 47.

As apparent in FIG. 7, when the support device 39 has been put off, the sheathing of the Bowden wire device can be pulled out at the distal end of the endoscope at least partially or entirely like the traction wire 13 of the Bowden wire device if a channel of the Bowden wire device exists. As illustrated in FIG. 7, the rear wall of the support device 39 facing the head of the endoscope forms a stop in the pushing direction opposite to the distal end of the sheathing of the Bowden wire device. Thus, apart from a fixed screw connection, the necessary connection between the sheathing of the endoscope and the endoscope for fastening the sheathing of the Bowden wire device in the longitudinal direction can also be achieved by simply inserting the support device 39; the sheathing of the Bowden wire device is limited in the direction of pulling at the proximal end by a stop which is not shown in greater detail and is limited in the direction of pushing at the distal end by the rear wall of the support device 39 and is thus securely fixed in its longitudinal direction.

Figure 8:
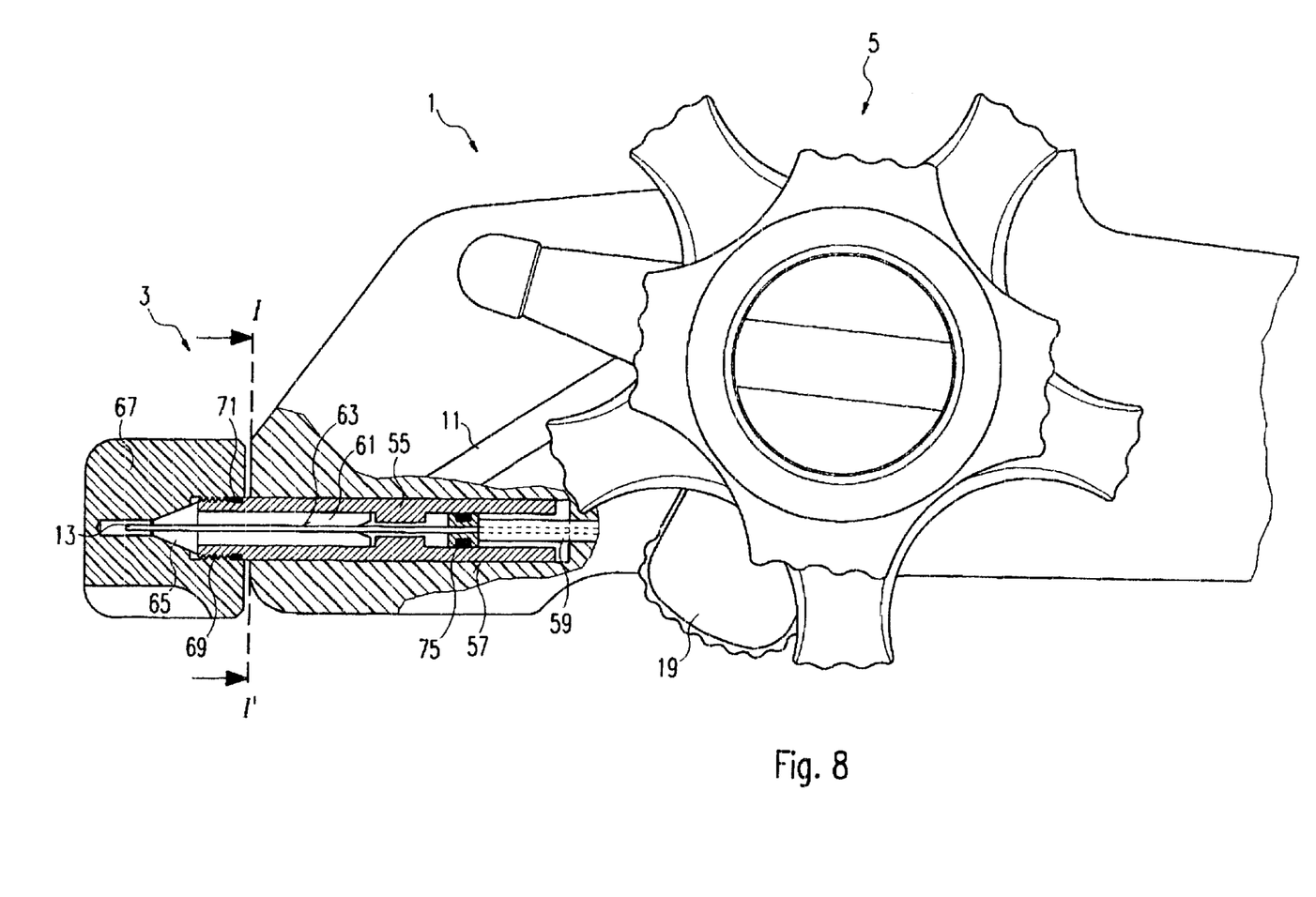
FIG. 8 shows a side view of a proximal end of an endoscope with a different embodiment of a quick-acting closure, in partial section.

FIG. 8 shows another embodiment according to the invention, in which the pivoting movement of the operating lever 19 is transformed into a movement in the longitudinal direction of the traction wire 13 of the Bowden wire device via the lever or the rod 11. For this purpose, as apparent from FIG. 9, the lever 11 is eccentrically mounted with one end thereof on the operating lever 19, e.g. by means of an axle 79 or a bolt, such that it is rotatable about an axis which is perpendicular to the plane of the drawing; with the other end, it is mounted on a partial portion of a slide 55 projecting outside e.g. by means of a screw 77 in such a way that it is rotatable about an axis perpendicular to the plane of the drawing. Thus, when the lever 19 is turned in the direction B in the longitudinal direction of the traction wire 13 of the Bowden wire device, the slide 55 is moved out of the proximal end 3 of the endoscope and is moved into it when the lever 19 is turned in the opposite direction.

Figures 9, 10, 11:
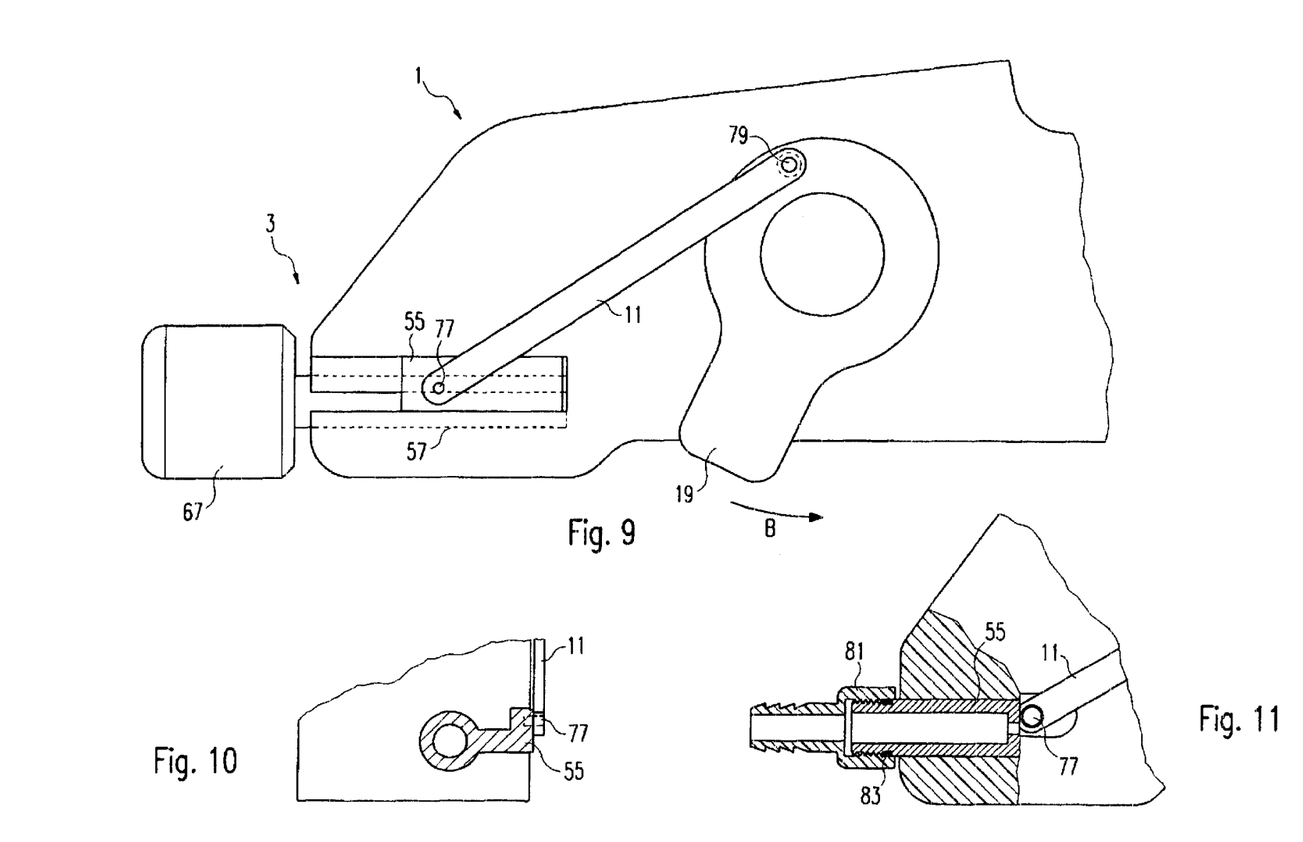
FIG. 9 shows a side view of a proximal end of an endoscope according to FIG. 8 without a control mechanism.
FIG. 10 shows a cross-sectional view along the line I–I' in FIG. 8.
FIG. 11 shows a side view of a proximal end of an endoscope according to FIG. 8 with an irrigation cap put thereon.

Here, by arranging the eccentric rod 11 correspondingly or by the distance of its mounting position 79 from the axis of rotation of the operating lever 19, the maximum movement or working area of the slide 55 can be selected to be larger than the actual movement area of the traction wire of the Bowden wire device or of the mechanism at the distal end of the endoscope connected therewith. Thus, a prestress can be exerted on the Bowden wire device as described above in connection with the first embodiment.

In the second embodiment shown, the quick-acting lever 3 which is pivotable or displaceable in the longitudinal direction of the traction wire 13 of the Bowden wire device is equipped with a clamping gripper 61, which can be clamped by means of a clamping element e.g. in the form of a clamping nut 67 in order to fixedly secure the end of the traction wire 13 guided in the clamping gripper 61 in the slide 55 in the longitudinal direction.

As illustrated in FIG. 8, the slide 55 may be configured to be substantially cylindrical and may comprise a projection shaped like the web of a key at its outer periphery which extends in the longitudinal direction at least over a part of its length. This slide 55 is located in a slot-shaped bore 57 at the proximal end of the endoscope in the longitudinal direction of the traction wire 13 of the Bowden wire device; the inner dimensions of this bore regarding the cross-section thereof are complementary to or slightly larger than the outer dimensions of the slide 55 so that the slide 55 can be moved easily in this bore 57 in the longitudinal direction of the traction wire 13 of the Bowden wire device.

For receiving the traction wire 13 of the Bowden wire device, the cylindrical portion of the slide 55 comprises a recess e.g. in the form of a bore in its end oriented in the distal direction, whose inner dimensions are large enough to receive the end of a Bowden wire device, e.g. a cylindrical projection of the housing, which serves as a stop or as an attachment for the sheathing of a Bowden wire device. In order to obtain a sealing effect that might be desirable, a sealing element—e.g. in the form of an O-ring—may be arranged between the inner wall of the bore of the slide 55 and the end of the Bowden wire device, which sealing element is optionally fixedly received in a ring-shaped recess of the bore of the slide 55 or, as shown in FIG. 8, in a ring-shaped recess at the end of the Bowden wire device. At the other end of the slide 55 projecting from the proximal end 3 of the endoscope, there is a recess, e.g. in the form of a bore, extending in the longitudinal direction of the traction wire 13 of the Bowden wire device as a receiving portion for a clamping gripper 61. As illustrated in the example, this bore may be limited in its depth, so the slide 55 comprises a mid-portion with a bore having a smaller diameter than these bores and having at least a slightly larger diameter than the outer diameter of the traction wire 13 of the Bowden wire device.

Hereby, it is possible to insert the slide 55 into the receiving portion 57 for the slide at the proximal end 3 of the endoscope; the proximal end of the traction wire 13 of the Bowden wire device moves through the recesses in the longitudinal direction inside the slide 55 and at least partly projects into the bore at the proximal end of the slide 55. In order to fix the end of the wire, the clamping gripper 61 is inserted into this bore, which receives the end of the traction wire 13 of the Bowden wire device in its central bore 63. In order to make it easier to introduce the end of the traction wire, the clamping gripper 61 may comprise a cone-shaped broadened portion at its opening oriented in the distal direction. At the proximal end, the substantially cylindrical clamping gripper 61 comprises a cone-shaped head 65 with e.g. four longitudinal slots. If a force is exerted onto this cone-shaped head 65 from outside, the slots make it possible to reduce the inner bore and thus to clamp the portion of the traction wire 13 located therein. As illustrated in the embodiment serving as an example, the force may be exerted by a clamping element e.g. in the form of a clamping nut which comprises a bore with a conical end or bottom, so the clamping gripper closes around the end of the traction wire 13 of the Bowden wire device if this clamping nut is pushed onto the cone-shaped head 65 of the clamping gripper in the longitudinal direction of the traction wire 13 of the Bowden wire device. The edge at the face of the proximal opening of the slide 55, which engages behind a peripheral shoulder of the cone head 65, serves as a limiting stop acting against this force in the distal direction. Likewise, however, it would be conceivable to form the limiting stop between the end of the clamping gripper 61 opposing the cone-shaped head 65 and the bottom of the bore at the proximal end of the slide 55.

As illustrated in FIG. 8, the projecting length of the end of the traction wire is to be selected such that, on the one hand, it can at least be fixedly enclosed by the clamping gripper 61 and on the other hand, it only projects from the clamping gripper to such an extent that the clamping nut 67 can be screwed on without squeezing the end of the wire. For this purpose, the clamping nut 67 may comprise a recess in the form of a bore which exceeds beyond the conical bottom in order to offer a larger receiving portion for the end of the traction wire of the Bowden wire device. If a sealing effect is desired between the traction wire 13 and the sheathing of the Bowden wire device, this bore does not go through the clamping nut 67, as shown in FIG. 8; the thread portion between the inner thread of the clamping nut 67 and the outer thread of the proximal end of the slide 55 may comprise a sealing element e.g. in the form of an O-ring 71.

Like in the first embodiment, with this embodiment, too, it is possible to exert a prestress onto the Bowden wire device; changing the prestress and thus the working area defined by the end positions 15', 15" is of course also possible during an operation. For this purpose, it is only necessary to loosen the attachment unit in the quick-acting closure 3, i.e. the clamping gripper 61, by loosening the clamping nut 67, or to loosen the lever 21 by actuating the turning knob 29 and to fix them again in a locking position different from this position inside or outside the previous working area by screwing on the clamping nut 67 or by lowering the lever 21 by actuating the turning knob 29.

In practice, this change of the working area already described above means that, in a way, the traction wire 13 of the Bowden wire device is grasped again, which can be done in both directions, so even in extreme situations, in which the position and thus the effective length of the traction wire 13 of the Bowden wire device in the endoscope changes due to extreme distortion, curving, bending etc. of the shaft and/or the head of the endoscope, one can react by correspondingly changing or adjusting the new working area.

FIG. 11 shows how an irrigation cap 81 can be placed, e.g. screwed, onto the end of the slide 55 projecting proximally for cleaning purposes; again, a sealing element 83 between the inner thread of the irrigation cap and the outer thread of the end of the slide ensures the liquid-tightness that is required for sufficient irrigation pressure. Thus, like in the first embodiment, it is possible for the operating personnel, e.g. a doctor or a doctor's assistant, to excellently clean the Bowden wire device and, particularly if the entire Bowden wire device is removed, the entire channel of the Bowden wire device without having to consult maintenance personnel or technicians, which would be expensive and time-consuming.

Instead of the type of attachment illustrated or instead of the clamping gripper 61 shown, it is of course also conceivable to use other types of attaching means which are displaceable in the longitudinal direction of the traction wire 13 of the Bowden wire device, e.g. a clamping gripper which is configured to be cone-shaped in the distal direction and which is pressed into a conical bore at the proximal end of the slide 55. Likewise, instead of a clamping nut 67, other clamping elements such as engaging levers, springs or the like are conceivable, too, which act upon the clamping gripper in the corresponding direction with a force closing the clamping gripper.

What is claimed is:

1. A flexible endoscope comprising:
    (a) a first quick-acting closure located at a proximal end of the endoscope and adapted to be displaceable within a closure working area between first and second closure end positions, the closure working area defining a traction wire working area for a traction wire of a Bowden wire device associated with the endoscope;
    (b) an attachment unit connected to the first quick-acting closure for selectively detaching the traction wire from the first quick-acting closure and attaching the traction wire to the first quick-acting closure;
    (c) a positioning structure associated with the first quick-acting closure and attachment unit, the positioning structure defining a locking position of the first quick-acting closure in which the attachment unit can be actuated; and
    (d) a mechanism at a distal end of the endoscope operatively connected to the traction wire, the mechanism being detachable from the remainder of the endoscope.

2. The endoscope of claim 1 wherein the locking position is remote from the first and second closure end positions.

3. The endoscope of claim 1 wherein the positioning structure includes an operating element for simultaneously actuating the attachment unit while defining the locking position of the first quick-acting closure.

4. The endoscope of claim 3 wherein the operating element comprises a turning knob connected to a cam for actuating the attachment unit.

5. The endoscope of claim 3 wherein the operating element includes a recess located along a portion of a periphery of the operating element, the recess adapted to be engaged by an engagement element connected at the proximal end of the endoscope.

6. The endoscope of claim 1 wherein the attachment unit includes a lever biased to exert a predetermined clamping force on the traction wire.

7. The endoscope of claim 1 wherein the first quick-acting closure comprises a clamping device which is displaceable in the longitudinal direction of the traction wire.

8. The endoscope of claim 7 wherein the clamping device comprises a slide with a clamping element and clamping gripper, the clamping element and clamping gripper operative to clamp the traction wire.

9. The endoscope of claim 1 further comprising an externally operable second quick-acting closure for selectively securing the mechanism at the distal end of the endoscope and releasing the mechanism from the distal end of the endoscope.

10. The endoscope of claim 9 wherein the second quick-acting closure comprises a snap-fit or locking closure.

11. The endoscope of claim 9 wherein the mechanism at the distal end of the endoscope is mounted in a support device connected to the remainder of the endoscope by the second quick-acting closure to provide a distal limiting stop for sheathing associated with the traction wire, so that, the sheathing is removable from the endoscope when the support device is detached from the endoscope.

12. The endoscope of claim 1 wherein the first quick-acting closure is moveable beyond its second end position to allow the end of the traction wire connected to the first quick-acting closure to slip through, and thereby release from, the attachment unit.

13. A flexible endoscope having a proximal control end and a distal end to which a mechanism is attached, the mechanism being actuated via a traction wire of a Bowden wire device associated with the endoscope, the endoscope comprising:

(a) a first quick-acting closure located at the proximal end of the endoscope and adapted to be displaceable within a closure working area between first and second closure end positions; and (b) an attachment unit connected to the first quick-acting closure for selectively detaching the traction wire from the first quick-acting closure while the endoscope is in use and reattaching the traction wire to the first quick-acting closure to redefine a working area for the traction wire.

14. The endoscope of claim 13 wherein the first quick-acting closure comprises a clamping device which is displaceable in the longitudinal direction of the traction wire.

15. The endoscope of claim 14 wherein the clamping device comprises a slide with a clamping element and clamping gripper, the clamping element and clamping gripper operative to clamp the traction wire.

16. The endoscope of claim 14 wherein the clamping device comprises a closure member pivotally connected to the proximal end of the endoscope, a lever pivotally connected to a distal end of the closure member, and a mechanism for pivoting the lever with respect to the pivot member to provide a clamping action for the traction wire between the lever and closure member.

17. The endoscope of claim 13 further comprising an externally operable second quick-acting closure for selectively securing the mechanism at the distal end of the endoscope and releasing the mechanism from the distal end of the endoscope.

18. The endoscope of claim 17 wherein the second quick-acting closure comprises a snap-fit or locking closure.

19. The endoscope of claim 17 wherein the mechanism at the distal end of the endoscope is mounted in a support device connected to the remainder of the endoscope by the second quick-acting closure to provide a distal limiting stop for sheathing associated with the traction wire, so that, the sheathing is removable from the endoscope when the support device is detached from the endoscope.

* * * * *